United States Patent
Tappel

(10) Patent No.: US 7,408,178 B2
(45) Date of Patent: Aug. 5, 2008

(54) METHOD FOR THE REMOVAL OF A MICROSCOPIC SAMPLE FROM A SUBSTRATE

(75) Inventor: Hendrik Gezinus Tappel, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 11/167,781

(22) Filed: Jun. 27, 2005

(65) Prior Publication Data

US 2006/0000973 A1    Jan. 5, 2006

(30) Foreign Application Priority Data

Jul. 1, 2004    (NL) .................. 04076893

(51) Int. Cl.
*H01J 37/244* (2006.01)
(52) U.S. Cl. ............... 250/492.21; 250/492.3
(58) Field of Classification Search ........... None
See application file for complete search history.

(56) References Cited

U.S. PATENT DOCUMENTS

| 5,270,552 | A  |   | 12/1993 | Ohnishi et al. |
| 6,420,722 | B2 |   | 7/2002  | Moore et al. |
| 6,570,170 | B2 |   | 5/2003  | Moore |
| 6,664,552 | B2 | * | 12/2003 | Shichi et al. ........... 250/492.21 |
| 6,781,125 | B2 | * | 8/2004  | Tokuda et al. ............... 250/310 |
| 6,870,161 | B2 |   | 3/2005  | Adachi et al. |
| 6,927,391 | B2 |   | 8/2005  | Tokuda et al. |
| 2006/0157341 | A1 |   | 7/2006  | Fuji |

FOREIGN PATENT DOCUMENTS

NL    1023657    12/2004

OTHER PUBLICATIONS

Shaw, Jonathan, Thinking Small, From quantum materials design to "voodoo physics" in the nanoscientists' weird world, Harvard Magazine, Jan.-Feb. 2005, p. 50-59.
Step 8- FIB-mill to Free Membrane from Trenches, http://fibics.com/SC_FIBTEBStep8.html.
Kendrick, Anthony B., Thomas M. Moore, Lyudmila Zaykova-Feldman, Mechanical Conversion for High-Throughput TEM Sample Preparation, Journal of Physics, Series 26, 2006, p. 227-230.
Kleindiek Nanotechnik, Increasing Sample Preparation Throughput.

* cited by examiner

*Primary Examiner*—David A. Vanore
(74) *Attorney, Agent, or Firm*—Scheinberg & Griner, LLP; David Griner; Michael O. Scheinberg

(57) ABSTRACT

The invention provides a method for the removal of a microscopic sample 1 from a substrate 2, comprising the steps of:
  performing a culling process whereby the substrate 2 is irradiated with a beam 4 such that the sample is cut out of the substrate, and
  performing an adhesion process whereby the sample 1 is adhered to a probe 3,
characterized in that
  the cutting process and the adhesion process overlap each other temporally.
By simultaneously carrying out the culling process and the adhesion process, a time-saving is realized as compared to a method in which these processes are performed sequentially.

16 Claims, 3 Drawing Sheets

METHOD FOR THE REMOVAL OF A MICROSCOPIC SAMPLE FROM A SUBSTRATE

Figure 1A:
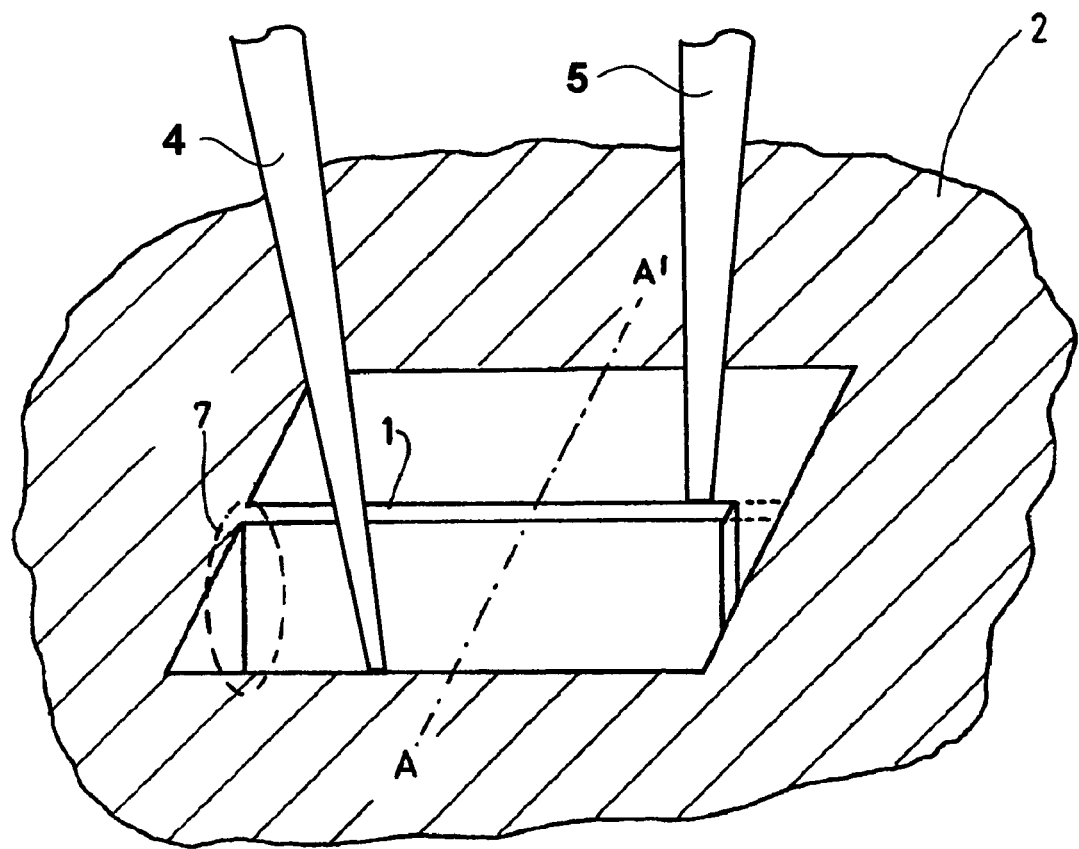

The invention pertains to a method for the removal of a microscopic sample from a substrate, comprising the steps of:
 performing a cutting process whereby the substrate is irradiated with a beam such that the sample is cut out of the substrate, and
 performing an adhesion process whereby the sample is adhered to a probe.

Such a method is known from the U.S. Pat. No. 5,270,552.

A method such as this is employed in particular in the semiconductor industry, where samples of microscopic proportions are taken out of substrates such as wafers in order to facilitate analysis and/or further processing. These days, such samples have dimensions of the order of magnitude of 10 μm at a thickness of 100 nm. A trend exists towards an even further size-reduction in the structures of interest, and, as a result hereof, a further size-reduction in the samples to be extracted.

The analyses which are made of such microscopic samples can be carried out, for example, with the aid of a TEM (Transmission Electron Microscope), SEM (Scanning Electron Microscope), SIMS (Secondary Ion Mass Spectroscope) or with X-Ray analysis equipment. The further manipulations can comprise, for example, making the sample thinner with the aid of an ion beam for the purposes of analysis with the aid of a TEM.

With the method described in the aforementioned patent document, a needle-shaped probe is moved by a manipulator to a position on a substrate where a sample is to be extracted. The sample is cut away from the substrate by removing material from two different directions with a focused ion-beam.

Prior to completely cutting the sample out of the substrate, the sample is adhered to the extremity of the probe by means of, for example, metal deposition. After the sample is completely cut away, the sample adhered to the probe is moved to another position with the aid of the manipulator.

It is to be noted that, prior to commencing the adhesion process, a portion of the cutting process must first be performed. After all, the presence of the needle-shaped probe causes shadow-formation; the presence of the probe will render a portion of the substrate invisible to the ion-beam deployed. For that reason, it is necessary to first commence the cutting process and then only move the probe to the sample position upon completion of the cutting in that region of the substrate that will come to lie in the shadow of the sample holder. Only when this is done can the adhesion process be started, whereupon the cutting process can be recommenced in order to completely extract the sample.

It is an aim of the invention to provide an alternative to the method such as mentioned in the known US patent document, which alternative provides for time-saving.

To that end, a method according to the invention is characterized in that the cutting process and the adhesion process overlap each other in time.

The invention is based on the insight that the adhesion of the sample to the probe will, in general, not be an instantaneous action. Adhesion using, for example, metal deposition or a glue is a process with a non-negligible duration, whereby, at a certain point, the connection which forms the adhesion is sufficiently strong to hold the sample against the pull of gravity. However, the connection is at that stage insufficiently strong to hold the sample if other forces arise. Such additional forces include, for example, the acceleration forces that arise attendant to the movement of and the manipulation of the sample, and the forces which occur attendant to the possible mechanical contacting ("collision") of the sample or the probe with other objects.

By overlapping the cutting process and the adhesion process in time, a time-saving is realized as compared to a method in which these processes are performed sequentially or where (at least portions of) the two processes are not carried out simultaneously.

In the method according to the invention, as soon as the connection is sufficiently strong to hold the sample against the pull of gravity, the sample is completely cut away. The connection is strengthened (overlapping temporally with the complete extraction) until it is sufficiently robust. The strengthening of the connection will generally continue after the sample has been completely cut away.

The strengthening of the connection can take the form of a metal deposition that increases over time (as is described in the aforementioned patent document), but it can also take the form of, for example, the continuing hardening of a glue.

It is also conceivable that the sample be first adhered to the probe with a less robust method—for example with electrostatic forces—after which a more robust adhesion is applied, using, for example, a glue or a metal deposition.

The method according to the invention further offers the possibility—while the adhesion process has not yet completed—of performing further manipulations on, for example, the sample, such as making the sample thinner. By performing these further manipulations coincidentally with the adhesion process (instead of sequentially), time-saving is also achieved.

It should be noted that yet another method for the extraction of a microscopic sample is known from U.S. Pat. No. 6,570,170. The method in this patent document differentiates itself from the previously mentioned known method in that here the adhesion of the sample to the probe occurs after the sample has been completely cut away. However, in this method too, the cutting process and the adhesion process are not carried out simultaneously, so that this method also fails to offer the time-saving offered by the method according to the invention.

In an embodiment of the method according to the invention adhering the sample to the probe comprises irradiating the sample with a beam.

In those instances of the method according to the invention whereby the adhesion of the sample takes place with the aid of irradiation, a second beam used to adhere the sample to the probe is present in addition to the cutting beam which extracts the sample.

It is to be noted that the beams do not have to be of the same type. For example, it is possible to use a beam of ions for cutting and a beam of photons, such as a laser beam, in order to harden and strengthen a glue.

In a further embodiment of the method according to the invention, cutting takes place—for at least a portion of the time—using two beams.

The probe will generally hinder the beam performing the extraction of the sample from reaching all of the substrate; shadow-forming occurs. It is therefore necessary to first partially cut-out the sample before moving the probe to the sample.

If use is made of two beams of a variety whereby both beams can be used for cutting, it is an attractive proposition to first remove material with both beams, and, at a point when shadowing effects of the probe are no longer to be feared, to then use one of the beams in order to adhere the sample to the probe. After all, by using both beams to perform cutting for at least a portion of the time, time-saving occurs when compared to the situation whereby only one beam is cutting.

It is to be noted that it is possible to change the function of an ion-beam from erosion (the removal of material) to deposition (the application of material) by changing properties of the beam, such as the current-density.

In a further embodiment of the method according to the invention, the orientation of the substrate in relation to the means which produce the cutting beam(s) remains unchanged during cutting.

Generally, in order to cut the sample away from the substrate, a wedge-shaped cut will have to be made. In the case of the use of a single beam, it will therefore be necessary to change the angle of incidence of the cutting beam with respect to the substrate. If, however, more than one beam is available, these beams will generally subtend an angle with respect to one another. Because of this, the sample can be completely cut away without changing the orientation of the substrate.

It is to be noted that a change in the orientation of the substrate with respect to the beam will usually imply a change in the position of the substrate. Because of this, changing the orientation will require a repositioning of the substrate with respect to the means which produce the beams.

The elimination of the need to reposition saves a non-negligible amount of time. After all, the repositioning of substrate and beam must occur with a high degree of accuracy. These days, a sample to be extracted will have dimensions of the order of magnitude of 10 μm at a thickness of 100 nm. Repositioning will therefore generally consist not only of moving the substrate, but also determining with sub-micron accuracy the position of the sample with respect to the means which produce both of the beams.

It is to be noted that in, in general, the beam is positioned with respect to the substrate with the aid of bending means. The orientation of the beam varies hereby slightly with respect to the substrate. However, this change of angle cannot generally be used to cut out the sample all around. After all, in order to cut away a wedge-shaped sample, it is a requirement that the beams intersect each other in the sample, a feat which is not easily achieved when the beams are bent by bending means that are placed outside the substrate.

In another embodiment of the method according to the invention, the aforementioned irradiation comprises irradiating with electrically charged particles.

In order to remove material, it is an attractive proposition to use, for example, a beam of ions. With this method, which is known per se, material can be removed with the desired positional accuracy, whereupon the extracted sample can then be analyzed.

It is to be noted that the beams do not have to be of the same type. For example, it is possible to use a beam of ions for cutting and to use a laser beam or an electron beam in order to harden and strengthen a glue.

It is also to be noted that the irradiation with electrically charged particles can occur coincident with, for example, the presence of special gases, whereby, for example, the cutting-speed of the beam(s) can be increased or the application of a metal deposition becomes possible.

In yet another embodiment of the method according to the invention, the aforementioned irradiation comprises irradiating with photons.

The adhesion of the sample to the probe can be enacted, for example, with the aid of a glue. The hardening of such a glue can be accelerated with a beam of, for example, photons, while the cutting can take place with, for example, an ion beam.

In yet another embodiment, the aforementioned irradiation comprises irradiating with a focused beam.

The method is used to locally extract a microscopic sample, whereby the damaging and disruption of the substrate material associated with the extraction process also occur only locally. It is therefore an attractive proposition, if not essential, to employ a focused beam.

Figure 1B:
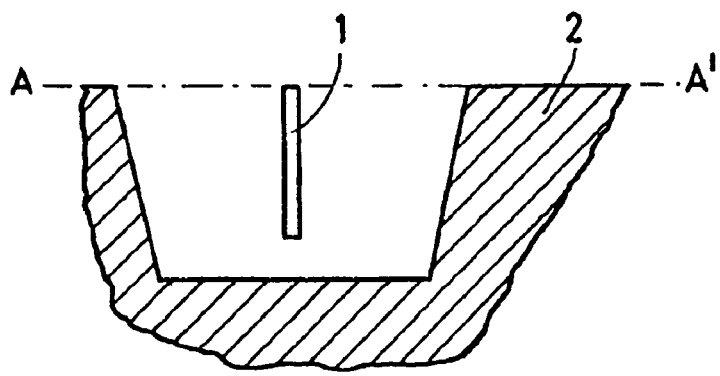
Figure 2:
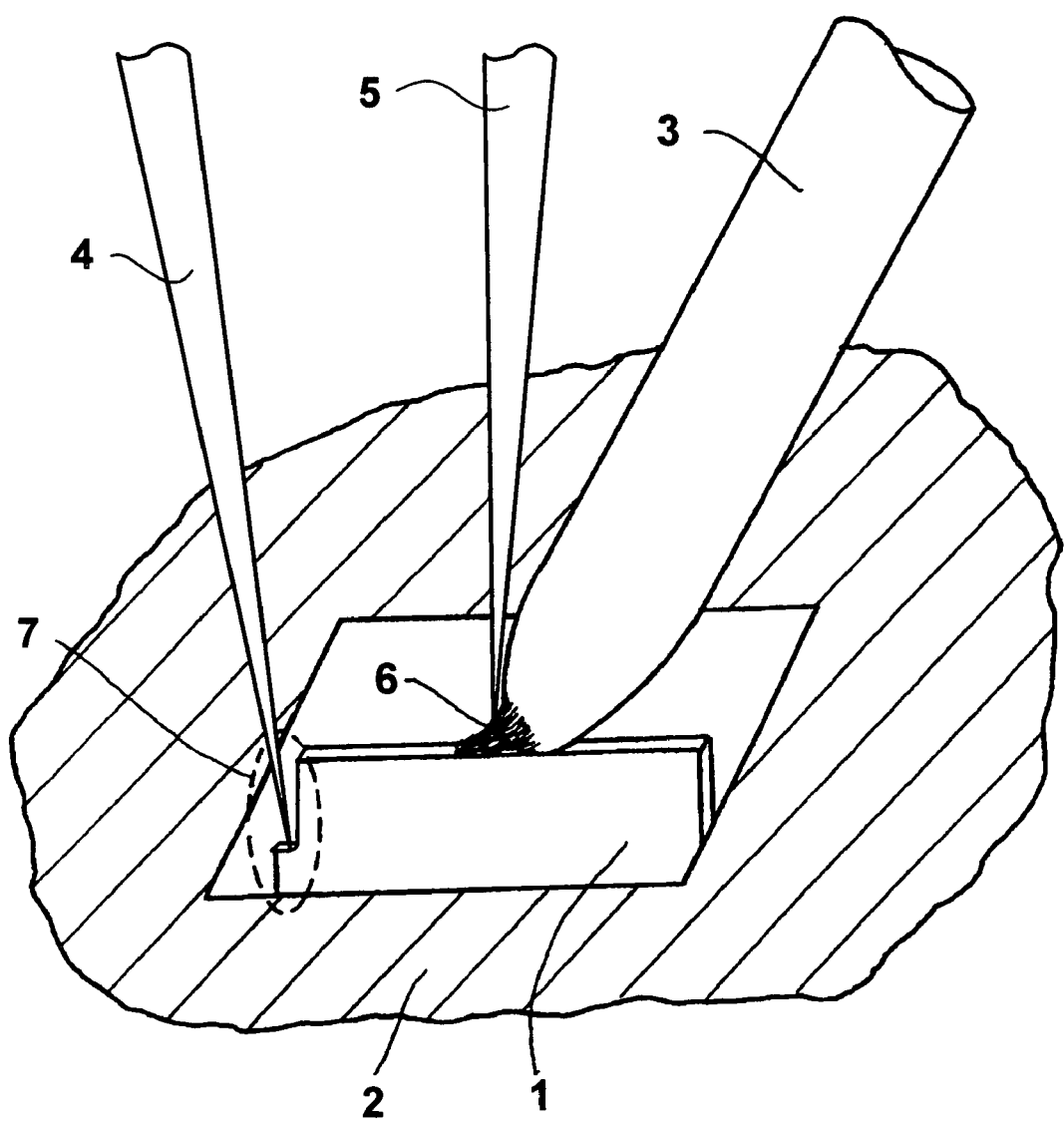
Figure 3:
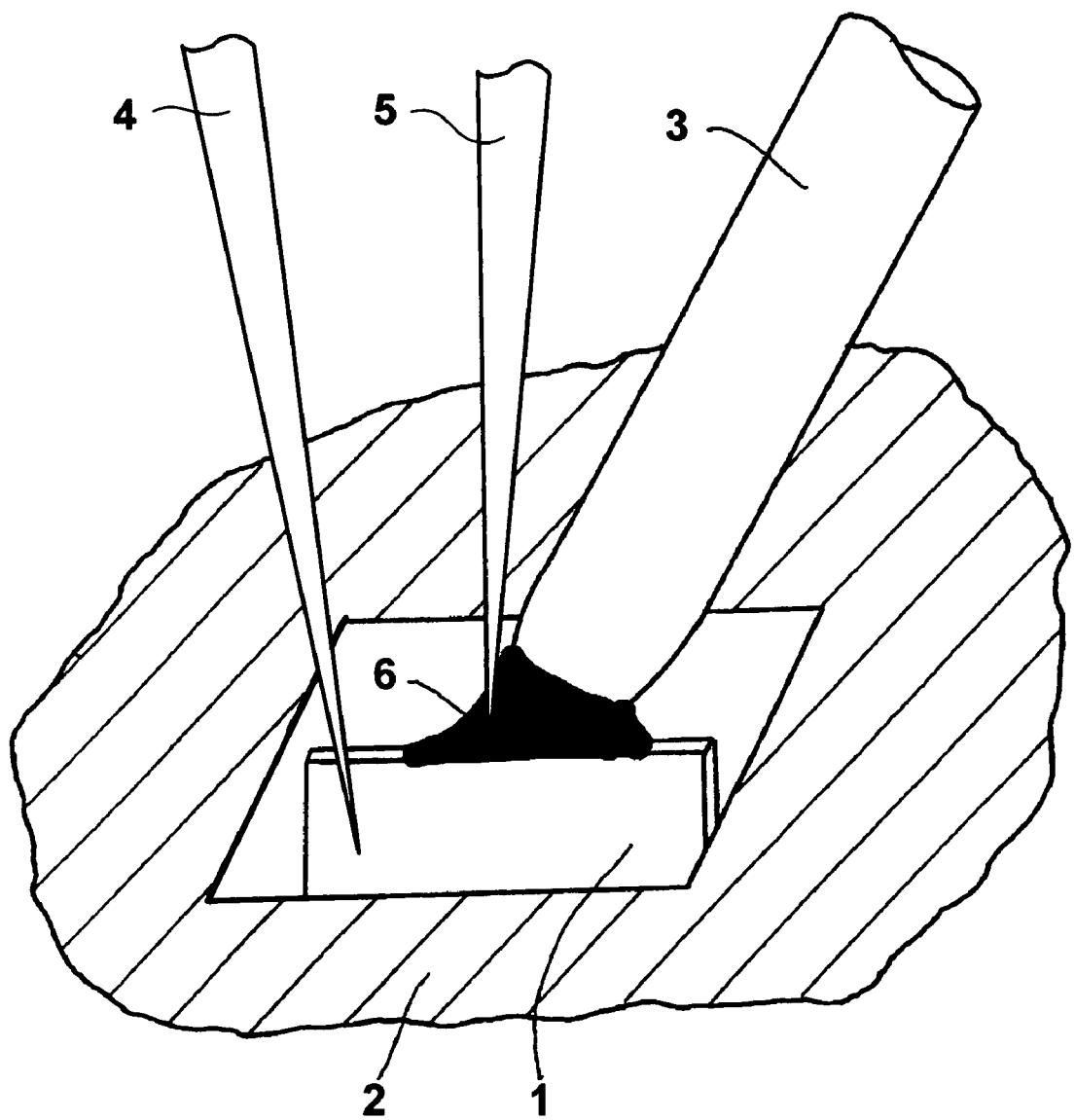

The invention will be further elucidated on the basis of figures, whereby corresponding elements are depicted using the same reference numbers. In this respect:

FIG. 1A is a schematic representation of a substrate from which a sample is cut away by two beams, FIG. 1B is a schematic representation of a cross-section from FIG. 1A, FIG. 2 is a schematic representation of a substrate with a partially cut-away sample that is affixed to a needle-shaped extremity of a probe, and, FIG. 3 is a schematic representation of a substrate with a completely cut-away sample to which a probe is affixed.

FIGS. 1A and 1B depict schematically a substrate in the form of a wafer 2 from which a sample 1 is cut away by two beams 4 and 5.

FIG. 1A shows how sample 1 is cut away by two ion beams 4 and 5 simultaneously. Because the two beams 4 and 5 exhibit an angle with respect to each other, it is possible to cut out the sample 1 all around without the wafer 2 having to assume another orientation with respect to the (non-depicted) means which produce the ion beams. In the situation shown, the bottom side of sample 1 is already largely cut away, whereupon the sample 1 will only remain connected to the wafer 2 by the connection 7 between the wafer 2 and the sample 1.

These days, a sample to be extracted will typically have dimensions of the order of magnitude of 10 μm (that is to say length perpendicular to line AA') and a thickness (that is to say dimension in the direction of line AA') of 100 nm.

FIG. 1B shows a cross-section according to line AA' depicted in FIG. 1A, whereby it can be clearly seen that the lower surface of sample 1 is free of the wafer 2.

FIG. 2 schematically depicts a sample 1 that is affixed to a needle-shaped extremity of the probe 3.

The cutting process in the depicted situation has sufficiently progressed so that no further shadow-effect of the probe 3 is to be feared. The needle-shaped extremity of the probe 3 is moved to the position of the sample 1 to be extracted. The sample 1 is joined to the probe 2 by irradiation with an ion beam 5, whereby a metal deposit 6 adheres the sample 1 to the probe 3. At the same time, the remaining connection 7 between the sample 1 and the wafer 2 is removed with ion beam 4.

FIG. 3 shows a schematic depiction of the extracted sample 1, whereby the connection 6 between sample 1 and probe 3 is further strengthened.

The sample 1 is completely cut away from the wafer 2. The force which is exerted on the connection 6, is caused, as long as the wafer 2 and the sample 1 are not moved, solely by the weight of the sample 1. Connection 6 is further strengthened by beam 5 until this connection is sufficiently robust to withstand greater forces than that caused merely by the weight of the sample 1. A further manipulation, such as a further thinning of the sample 1, can concurrently take place with beam 4 while beam 5 is strengthening the connection 6.

The invention claimed is:

1. A method for the removal of a microscopic sample from a substrate, comprising the steps of:

performing a cutting process whereby the substrate is irradiated with a beam such that the sample is cut out of the substrate, and performing an adhesion process whereby the sample is adhered to a probe, characterized in that the cutting process and the adhesion process overlap each other temporally.

2. A method according to claim 1, whereby the adhesion process comprises irradiating the sample with a beam.

3. A method according to claim 2, whereby the cutting process during at least a portion of the duration of the cutting process is carried out by two beams simultaneously.

4. A method for the removal of a microscopic sample from a substrate, comprising the steps of:

performing a cutting process whereby the substrate is irradiated with a beam such that the sample is cut out of the substrate, whereby the cutting process during at least a portion of the duration of the cutting process is carried out by two beams simultaneously, and performing an adhesion process whereby the sample is adhered to a probe, whereby the adhesion process comprises irradiating the sample with a beam, whereby the cutting process and the adhesion process overlap each other temporally and the orientation of the substrate in relation to the means which produce the cutting beams remains unchanged during the cutting process.

5. A method according to claim 1, whereby the irradiation comprises irradiating with electrically charged particles.

6. A method according to claim 1, whereby the irradiation comprises irradiating with photons.

7. A method according to claim 1, whereby the irradiation comprises irradiating with a focused beam.

8. A method according to claim 2, whereby the irradiation comprises irradiating with electrically charged particles.

9. A method according to claim 3, whereby the irradiation comprises irradiating with electrically charged particles.

10. A method according to claim 4, whereby the irradiation comprises irradiating with electrically charged particles.

11. A method according to claim 2, whereby the irradiation comprises irradiating with photons.

12. A method according to claim 3, whereby the irradiation comprises irradiating with photons.

13. A method according to claim 4, whereby the irradiation comprises irradiating with photons.

14. A method according to claim 2, whereby the irradiation comprises irradiating with a focused beam.

15. A method according to claim 3, whereby the irradiation comprises irradiating with a focused beam.

16. A method according to claim 4, whereby the irradiation comprises irradiating with a focused beam.

* * * * *